US011484417B2

(12) United States Patent
Joo (10) Patent No.: US 11,484,417 B2
(45) Date of Patent: Nov. 1, 2022

(54) ACETABULAR CUP REMOVING APPARATUS FOR ARTIFICIAL HIP JOINT

(71) Applicant: IMEDICOM, Gunpo-si (KR)

(72) Inventor: Don Soo Joo, Gunpo-si (KR)

(73) Assignee: IMEDICOM, Gunpo-si (KR)

( * ) Notice: Subject to any disclaimer, the term of this patent is extended or adjusted under 35 U.S.C. 154(b) by 226 days.

(21) Appl. No.: 16/634,117

(22) PCT Filed: Aug. 14, 2018

(86) PCT No.: PCT/KR2018/009308
§ 371 (c)(1),
(2) Date: Jan. 24, 2020

(87) PCT Pub. No.: WO2019/039786
PCT Pub. Date: Feb. 28, 2019

(65) Prior Publication Data
US 2020/0205998 A1    Jul. 2, 2020

(30) Foreign Application Priority Data

Aug. 23, 2017 (KR) .................. 10-2017-0106590
Aug. 14, 2018 (KR) .................. 10-2018-0094672

(51) Int. Cl.
*A61F 2/46*     (2006.01)
*A61B 17/16*    (2006.01)

(52) U.S. Cl.
CPC ........ *A61F 2/4609* (2013.01); *A61B 17/1666* (2013.01); *A61F 2002/4619* (2013.01); *A61F 2002/4628* (2013.01)

(58) Field of Classification Search
CPC .... A61F 2/4609; A61F 2/4612; A61F 2/4603; A61F 2/46; A61F 2002/4619; A61F 2002/4627; A61F 2002/4628; A61F 2002/4625
See application file for complete search history.

(56) References Cited

U.S. PATENT DOCUMENTS

| 3,943,916 | A  | * | 3/1976  | Vadas    | A61B 17/32053 600/564 |
| 6,626,913 | B1 | * | 9/2003  | McKinnon | A61F 2/367 606/86 R   |
| 2015/0196402 | A1 | * | 7/2015  | Kim      | A61F 2/4609 606/81 |
| 2015/0359641 | A1 | * | 12/2015 | Nic      | A61B 17/1666 606/81 |

FOREIGN PATENT DOCUMENTS

KR      1020170015095 A     2/2017

* cited by examiner

*Primary Examiner* — Amy R Sipp
(74) *Attorney, Agent, or Firm* — Rabin & Berdo, P.C.

(57) ABSTRACT

The present invention relates to an acetabular cup removing apparatus for an artificial hip joint. An acetabular cup removing apparatus for an artificial hip joint according to one embodiment of the present disclosure comprises: a main driving unit; a main shaft which is rotatable by a driving force of the main driving unit; a cutter unit which is disposed at a front end of the main shaft, tiltable along an acetabular portion into which an acetabular cup has been implanted, and cuts the acetabular portion while being rotated by the main shaft; and a stepless adjustment unit for steplessly adjusting a tilting angle of the cutter unit while continuously moving in a forward and backward direction relative to the main shaft.

6 Claims, 10 Drawing Sheets

PRIOR ART

ACETABULAR CUP REMOVING APPARATUS FOR ARTIFICIAL HIP JOINT

TECHNICAL FIELD

The present disclosure relates to an acetabular cup removing apparatus for an artificial hip joint.

BACKGROUND ART

In general, an artificial hip joint is a substitute for a hip joint, which is used when trouble occurs in the function of the hip joint and can be implanted in the place of hip joint to maintain normal activity of the hip joint.

Such artificial hip joint is divided into an acetabular cup in a hemispherical shape inserted into the acetabular region of the pelvis and having a liner serving as a bearing, a stem fitted into the femur, and a femoral head in a hemispherical shape provided at an end of the stem as a substitute for the femoral head and inserted into the acetabular cup.

Therefore, for patients with pain in the hip joint that is not functioning properly due to arthritis or dysplasia, trauma or infection sequelae, the hip joint experiencing the pain can be replaced with the artificial hip joint described above to thus restore the mobility of the joint and eliminate the pain.

Meanwhile, the artificial hip joint wears out as it is used for a long of time. Particularly, the acetabular cup rubbing against the head has a high incidence of abrasion due to continuous use of the joint, and if the abrasion continues, in a severe case, osteolysis occurs around the acetabular region of the pelvis where the acetabular cup inserted. Therefore, techniques for removing the previously inserted acetabular cup from the acetabular region of the pelvis have been continuously developed.

Figure 8:
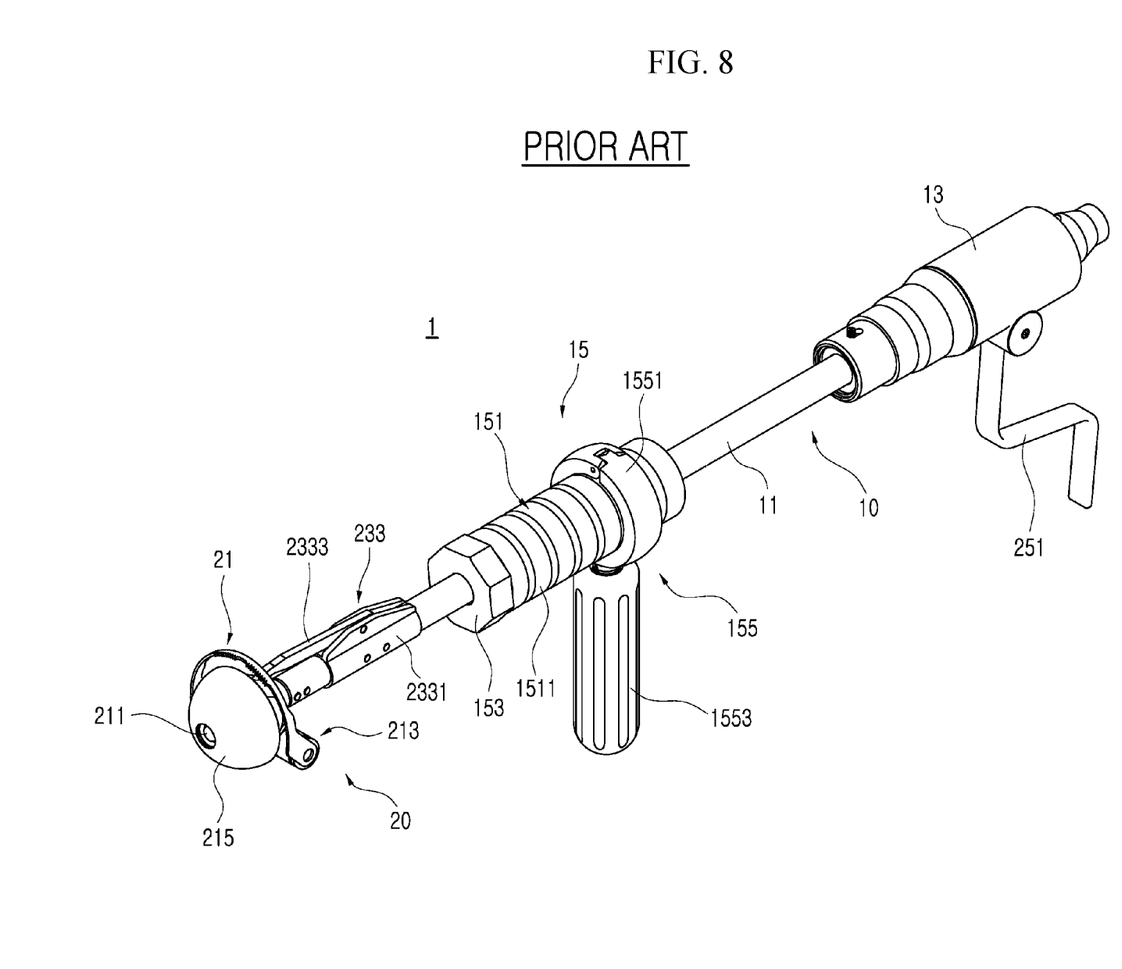
FIG. 8 shows a related acetabular cup removing apparatus for an artificial hip joint.
Figure 9:
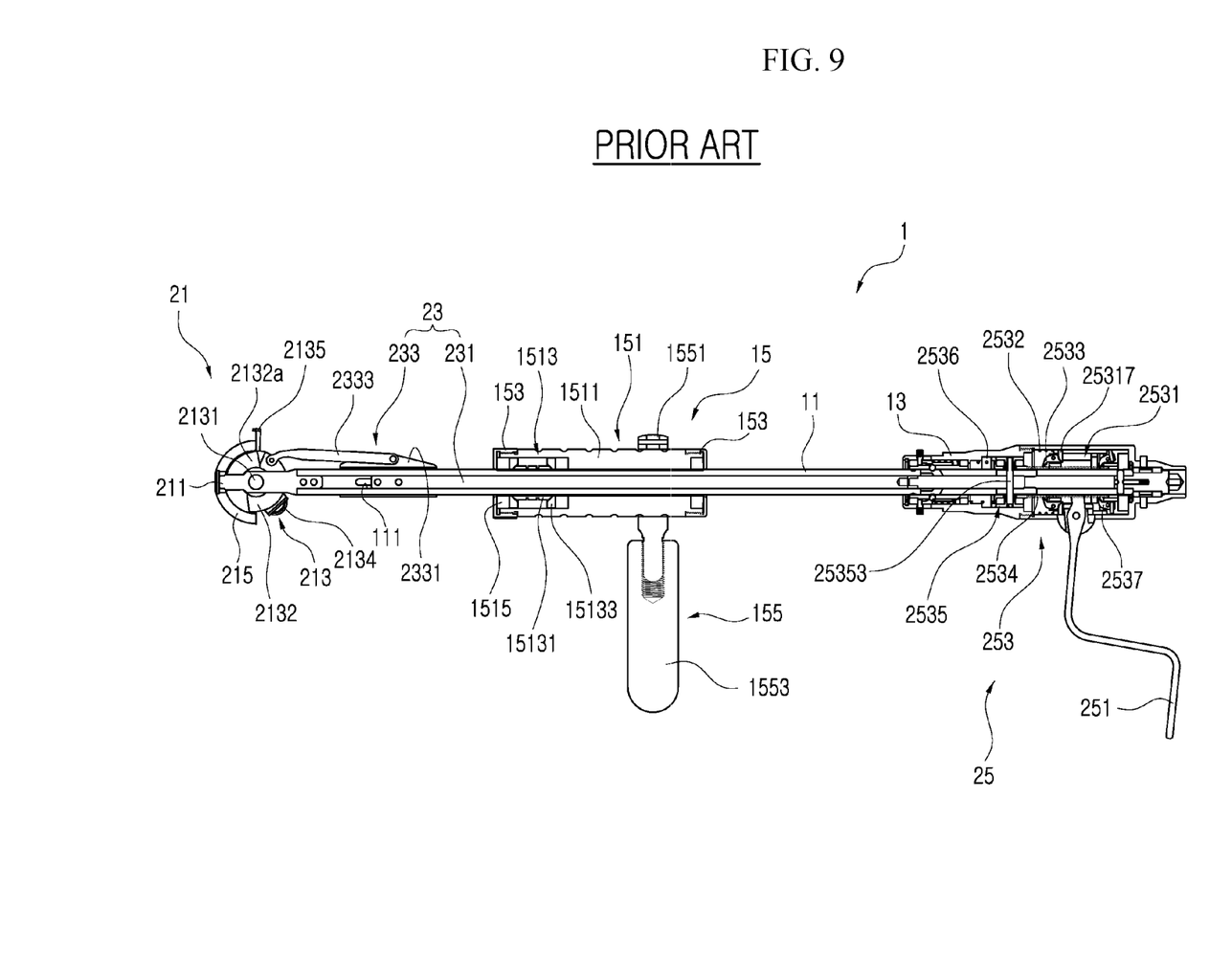
FIG. 9 is a schematic cross-sectional view of the acetabular cup removing apparatus for an artificial hip joint of FIG. 8.
Figure 10:
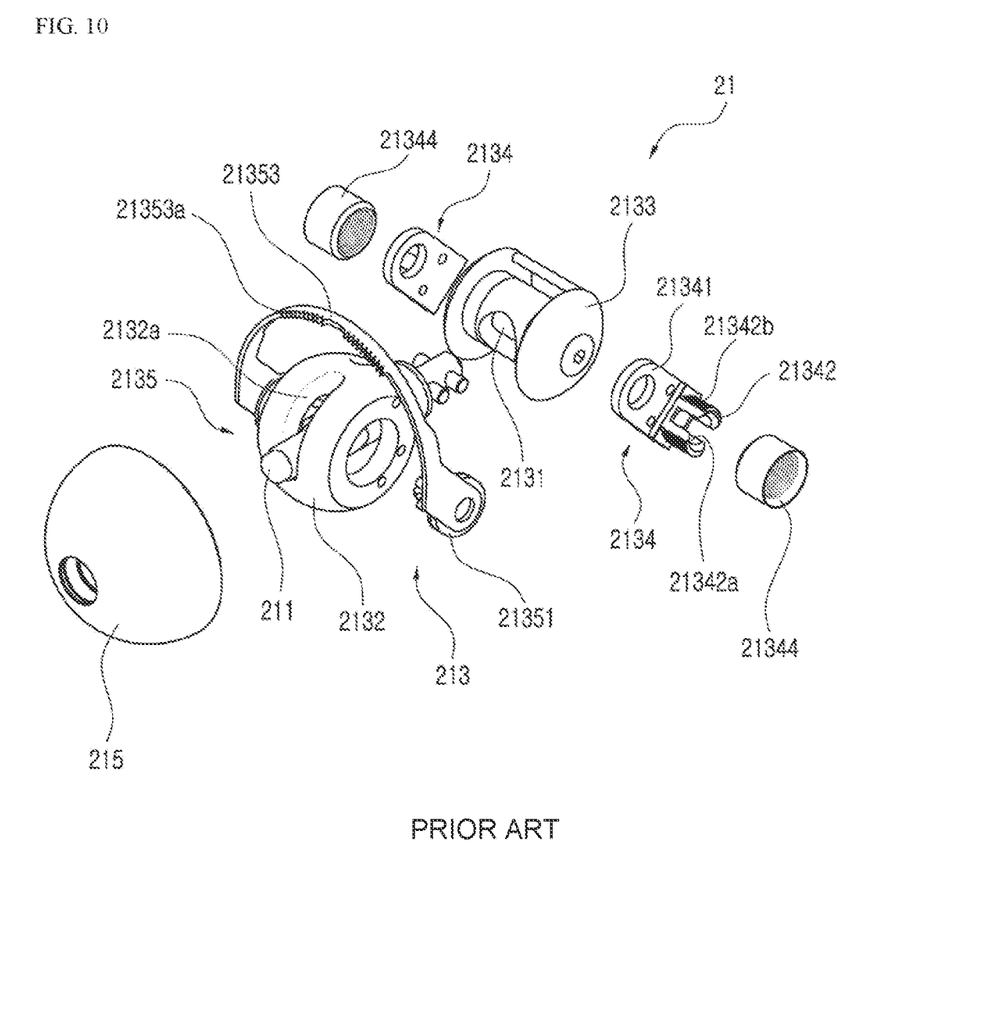
FIG. 10 schematically shows a disassembled state of the pivoting cutter of the acetabular cup removing apparatus for an artificial hip joint of FIG. 8.

In this regard, the present applicant has developed an acetabular cup removing apparatus for an artificial hip joint disclosed in Korean Patent Publication No. 10-2017-0015095. FIGS. 8 to 10 show the acetabular cup removing apparatus and these drawings correspond to FIGS. 2, 3 and 4 of the Korean Patent Publication, respectively. For convenience, reference numerals have been used as they are without changes.

The related acetabular cup removing apparatus includes a body part that rotates with power transmitted thereto, and a cutting part that is brought into close contact with the inner circumferential surface of the acetabular cup and rotates together with the body part to cut the acetabular portion to which the acetabular cup is attached. In particular, the cutting part includes a pivoting cutter that cuts the acetabular portion to which the acetabular cup is attached while rotating together with the body part, and an angle adjusting unit that adjusts the rotational angle of the pivoting cutter such that the pivoting cutter cuts the acetabular portion along the shape of the acetabular cup. Here, the angle adjusting unit includes an adjustment lever disposed inside a housing part and rotatable to the front or rear side, and an adjustment part that is moved to the front side in three steps in accordance with the rotation of the adjustment lever, thus rotating the pivoting cutter sequentially at a predetermined angle, and is returned to the original position after all three steps of movement are completed.

However, since the related acetabular cup removing apparatus for an artificial hip joint has a limit in which the pivoting cutter is angle-adjusted in three steps, there occurs time difference between steps, which results in uneven surface of the acetabular cut. In addition, when the portion of the acetabular in need of more cutting is in the step transitioning section, there is a problem that the pivoting cutter cannot be located in that portion.

In addition, the conventional acetabular cup removing apparatus for an artificial hip joint has a configuration in which the pivoting cutter returns to the original position only after all three steps of angle adjustment are completed. Therefore, since the pivoting cutter has to be adjusted again after all three steps of angle adjustment are completed and the pivoting cutter is returned to the original position in order to adjust the angle of the pivoting cutter to the previous angle, there is a problem that it is inconvenient to use and it also takes much time for the procedure.

DETAILED DESCRIPTION OF INVENTION

Technical Problem

The technical problem of the present disclosure is to provide an acetabular cup removing apparatus for an artificial hip joint, which ensures an even surface of an acetabular portion after cutting and which enables to directly adjust a tilting angle of a cutter to its previous angle and also enables to place the cutter directly to a place in need of more cutting of the acetabular portion.

Technical Solution

In order to achieve the above object, an acetabular cup removing apparatus for an artificial hip joint according to an embodiment of the present disclosure may include: a main driving unit; a main shaft which is rotatable by a driving force of the main driving unit; a cutter unit which is disposed at a front end of the main shaft, tiltable along an acetabular portion into which an acetabular cup has been implanted, and cuts the acetabular portion while being rotated by the main shaft; and a stepless adjustment unit for steplessly adjusting a tilting angle of the cutter unit while continuously moving in a forward and backward direction relative to the main shaft.

In addition, the stepless adjustment unit may include a slider movable relative to the main shaft on an outer peripheral surface of the main shaft in a forward and backward direction, a handle fixing clamp of which a front end is connected with a rear end of the slider in a manner in which the rear end of the slider does not fall out, wherein the handle fixing clamp is movable relative to the main shaft, and a power transmission member for tilting the cutter unit by transmitting a moving force of the slider.

The stepless adjustment unit may further include a bearing part for allowing the main shaft and the slider to rotate smoothly relative to the handle fixing clamp.

In addition, a rear cover may be located at a rear end of the handle fixing clamp to support the handle fixing clamp so that the handle fixing clamp is kept from being pushed backward and the rear cover is fixed to the main shaft.

In addition, the power transmission member may include a power transmission member body part surrounding the main shaft while being slidable relative to the main shaft, and a power transmission arm pivotably connected at one end to the power transmission member body part and pivotably connected at the other end to the cutter unit to tilt the cutter unit.

In addition, the power transmission member further includes an elastic supporting part for elastically supporting the power transmission member body part with respect to the main shaft.

In addition, the elastic supporting part may include a hollow part formed on the main shaft in a longitudinal direction thereof, a guide groove formed to penetrate a side of the main shaft and communicates with the hollow part, an elastic body inserted into the hollow part, and a connection member for connecting the power transmission member body part with the elastic body through the guide groove.

In addition, one end of the hollow part may be kept in a closed state, one end of the elastic body may be supported by the one end of the hollow part, and the other end of the elastic body may be supported by the connection member.

In addition, the cutter unit may include a cutter and a cutter tilting unit for tilting the cutter, and the cutter tilting unit may include a first tilting member connected to a front end of the main shaft and including a hinge hole in a direction orthogonal to an axial direction of the main shaft, a second tilting member rotatably inserted into the hinge hole and to which the other end of the power transmission arm pivotably connected, and a connection bracket connected at one end to the second tilting member and connected at the other end to the cutter to form a cutting trajectory corresponding to the acetabular portion while the main shaft is being rotated and the cutter is being tilted.

In addition, the bearing part may include, at a front portion of the handle fixing clamp, a first bearing disposed between the handle fixing clamp and the slider, and a second bearing disposed between the handle fixing clamp and the main shaft; and at a rear portion of the handle fixing clamp, a third bearing disposed between the handle fixing clamp and the main shaft; and a thrust bearing disposed between the handle fixing clamp and the main shaft.

In addition, the slider and the power transmission member may be integrally formed.

Advantageous Effects

As described above, the acetabular cup removing apparatus for an artificial hip joint according to the embodiment of the present disclosure may have the following effects.

According to the present disclosure, the stepless adjustment unit can steplessly adjust the tilting angle of the cutter while continuously moving in a forward and backward direction along the main shaft, and unlike the conventional one, there is no steps divided, thereby ensuring even cutting of the surface of the acetabular portion.

In addition, by moving the stepless adjustment unit in the forward and backward direction, the cutter can be located directly at a position requiring more cutting of the acetabular portion, and the tilting angle of the cutter can be adjusted to the immediately previous angle, thereby ensuring ease of use and shortened procedure time.

DETAILED DESCRIPTION

Hereinafter, preferred embodiments of the present disclosure will be described in detail with reference to the accompanying drawings. However, the description proposed herein is just a preferable example for the purpose of illustrations only, and not intended to limit the scope of the disclosure, so it should be understood that other equivalents and modifications could be made thereto without departing from the scope of the disclosure. For reference, the present disclosure relates to a stepless adjustment unit configuration newly conceived from the previous acetabular cup removing apparatus for an artificial hip joint invented by the present applicant in order to solve the above problems. Therefore, hereinafter, elements related to this will be described in detail, while the rest elements will not be described or described briefly as these are irrelevant to the subject matter of the present disclosure.

As shown in FIGS. 1 to 6, an acetabular cup removing apparatus 100 for an artificial hip joint according to an embodiment of the present disclosure includes a power tool 180 comprising a main driving unit 110, a main shaft 120, a cutter unit 150, a stepless adjustment unit 140, a battery 112 and a first handle 160.

Figure 1:
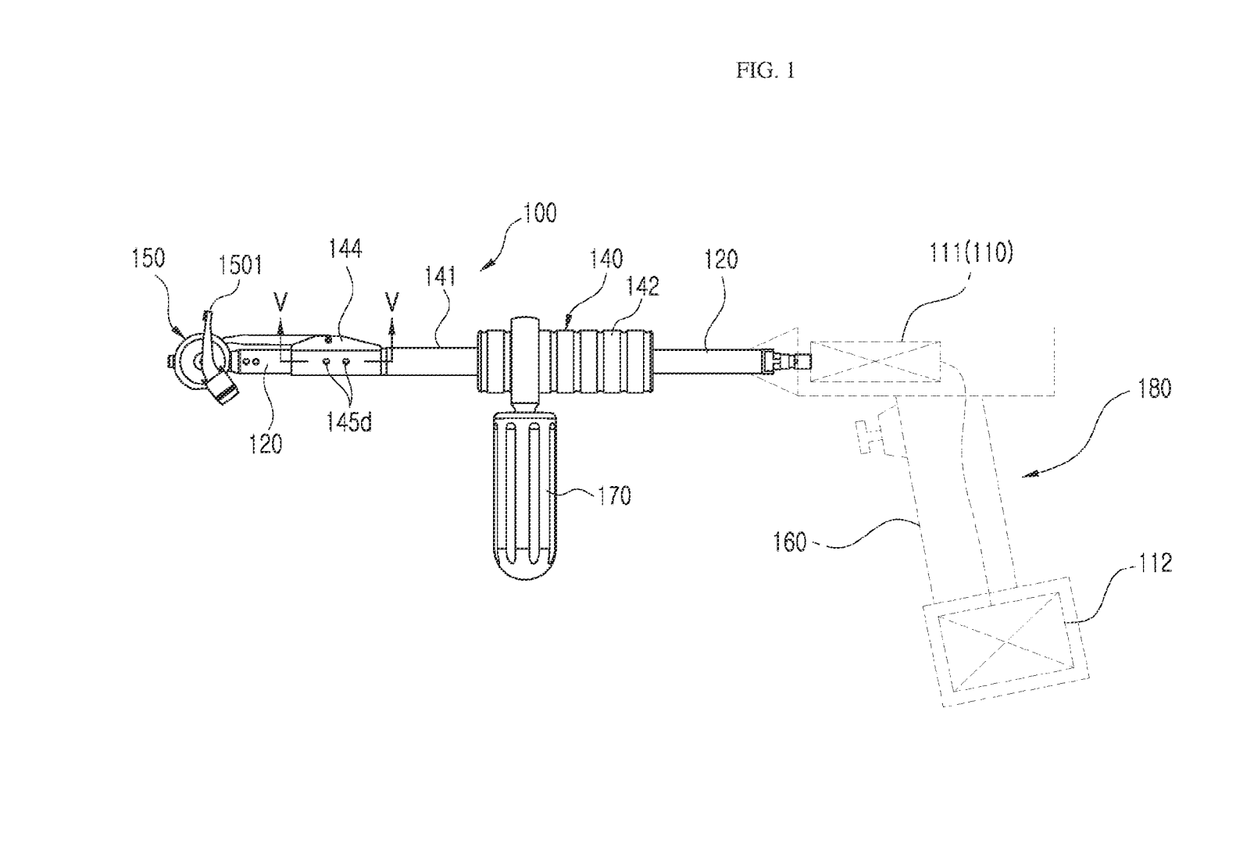
FIG. 1 is a front view schematically showing an acetabular cup removing apparatus for an artificial hip joint according to an embodiment of the present disclosure.

As shown in FIG. 1, the main driving unit 110 is an element provided to rotate the main shaft 120. For example, the main driving unit 110 includes a rotation motor 111 and a battery 112 for supplying power to the rotation motor 111. Therefore, when the main driving unit 110 is driven, the cutter unit 150 provided at a front end of the main shaft 120 may be rotated around the main shaft 120. Meanwhile, the main driving unit 110 may be provided within a first handle 160.

The main shaft 120 is an element that transmits the driving force of the main driving unit 110 to the cutter unit 150, and may have a predetermined length to allow the cutter 130 to reach the acetabular portion while the operator is in the state of holding the acetabular cup removing apparatus 100 for an artificial hip joint of the present disclosure. In addition, as shown in FIG. 1, the first handle 160 is provided at a rear end of the main shaft 120, and a second handle 170 is provided at the middle portion of the main shaft 120. The operator may hold the first handle 160 with one hand and grab the second handle 170 with the other hand to support the main shaft 120. Meanwhile, in order to support a smooth rotation of the main shaft 120 during its rotation, a bearing part 143 may be provided between the main shaft 120 and the stepless adjustment unit 140, which will be described below.

Figure 2:
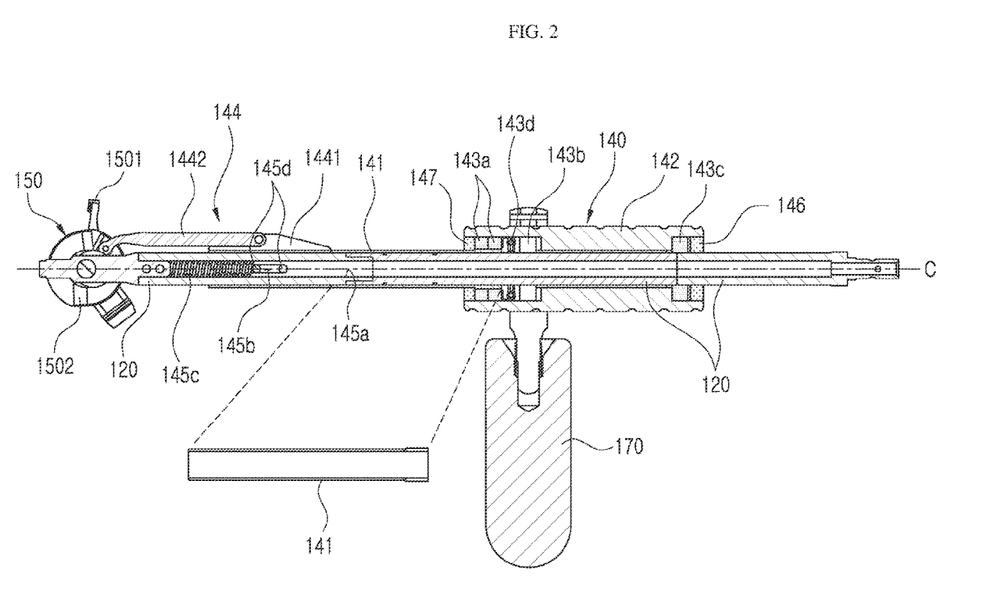
FIG. 2 is a cross-sectional view schematically showing a main part of the acetabular cup removing apparatus for an artificial hip joint of FIG. 1.
Figure 6:
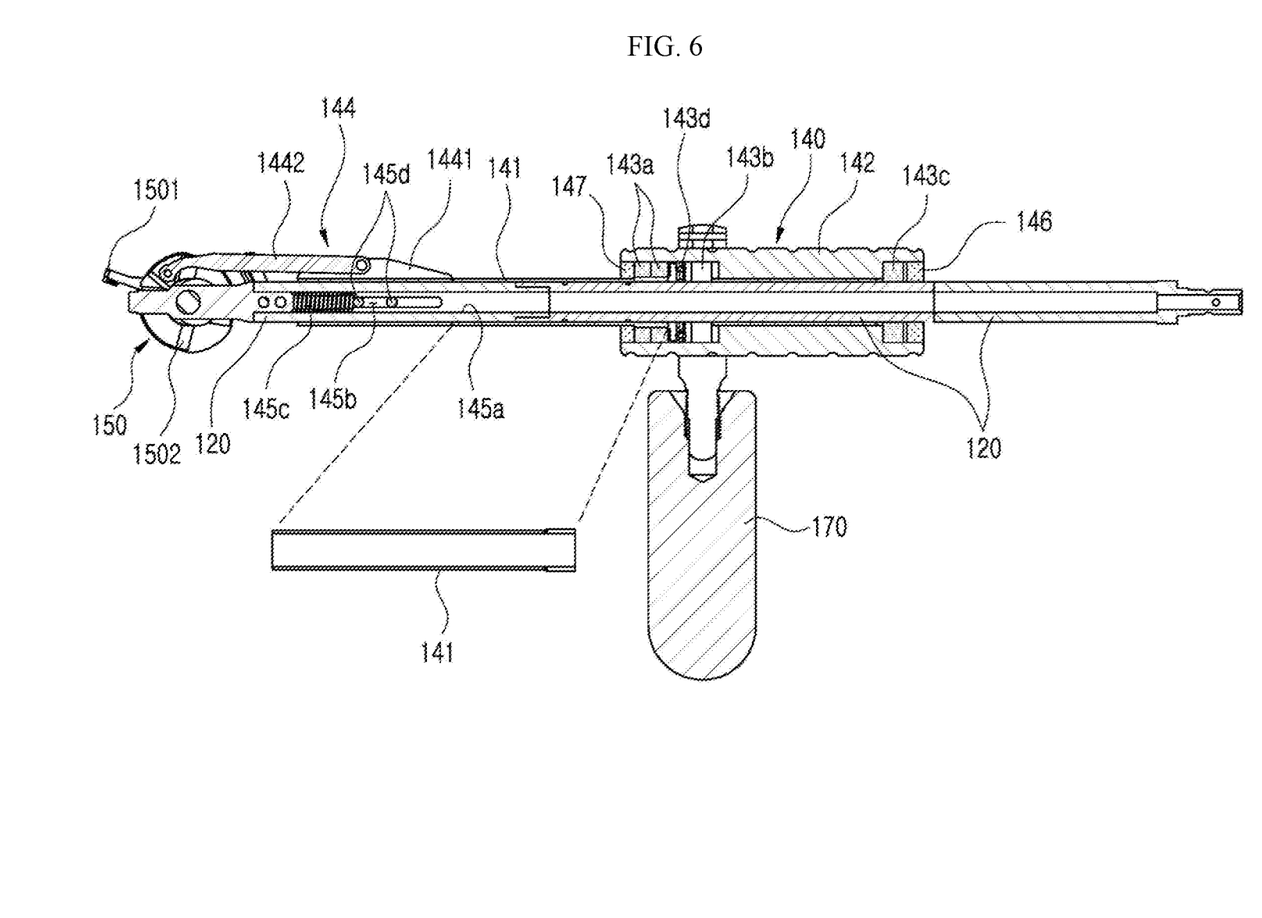
FIG. 6 is a cross-sectional view schematically showing the rotating cutter of the acetabular cup removing apparatus for an artificial hip joint of FIG. 2 at the adjusted angle.
Figure 7:
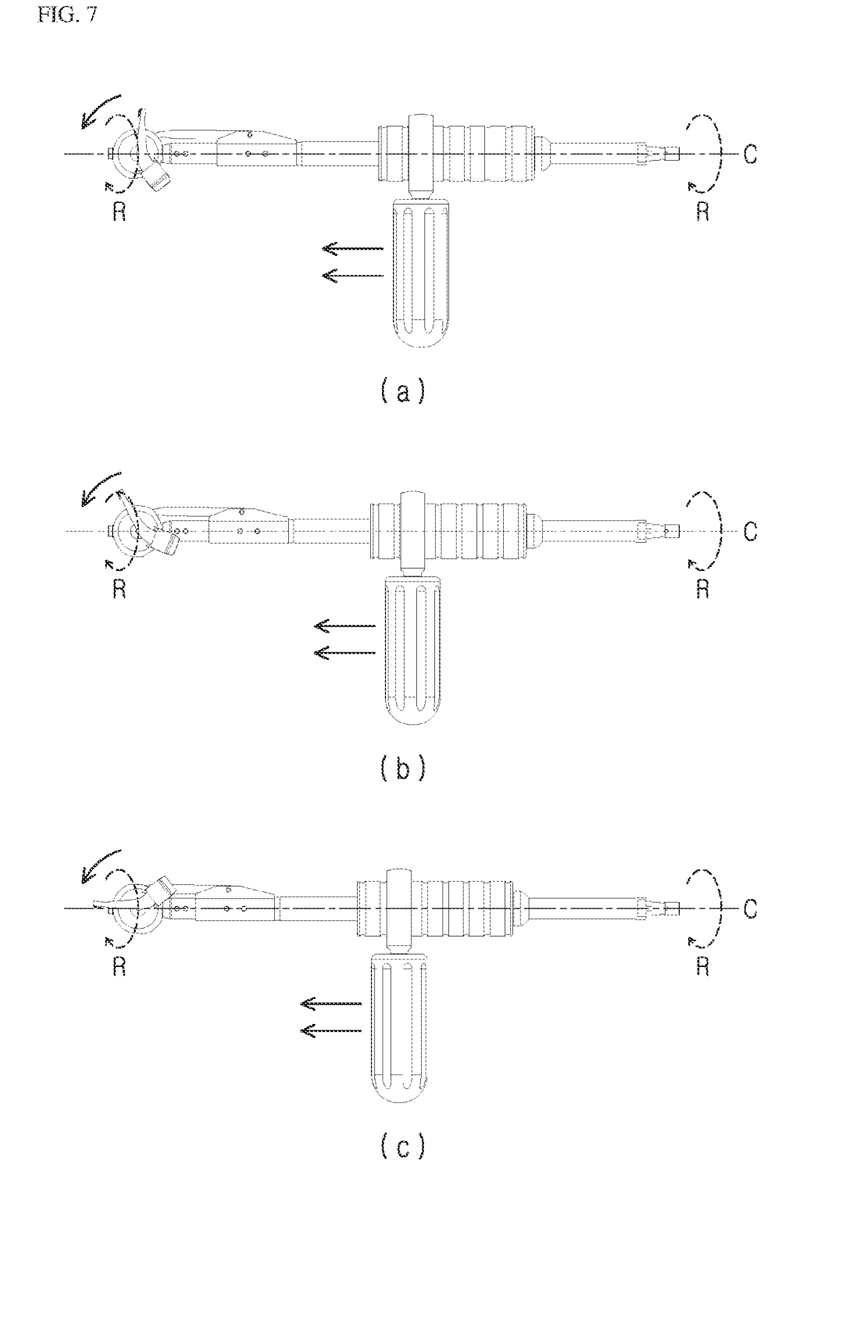
FIG. 7 is an exemplary view showing an operating state of the acetabular cup removing apparatus for an artificial hip joint of FIG. 1, sequentially showing a state of tilting a cutter by moving a stepless adjustment unit 140 forward.

The cutter unit 150 includes a cutter 1501 and a cutter tilting unit 1502 for tilting the cutter 1501, and is an element that substantially cuts the acetabular portion, and is similar in configuration to the cutter of the acetabular cup removing apparatus for an artificial hip joint disclosed in Korean Patent Publication No. 10-2017-0015095 by the present applicant. That is, as shown in FIGS. 1, 2 and 6, the cutter unit 150 may be provided at the distal end portion of the main shaft 120 and may be provided to be tiltable along the acetabular portion into which the acetabular cup is implanted. Therefore, the cutter unit 150 may be rotated around the main shaft 120 as a central axis according to the rotation of the main shaft 120 and tilted along the acetabular portion, while cutting the acetabular portion. The cutter unit 150 may cut the acetabular portion by rotating around an imaginary extension line C of a longitudinal axis of the main shaft 120 while being rotated by the main shaft 120. See FIG. 2. See also FIG. 7, showing a direction of rotation R about the imaginary extension line C of the longitudinal axis of the main shaft 120.

Figure 3:
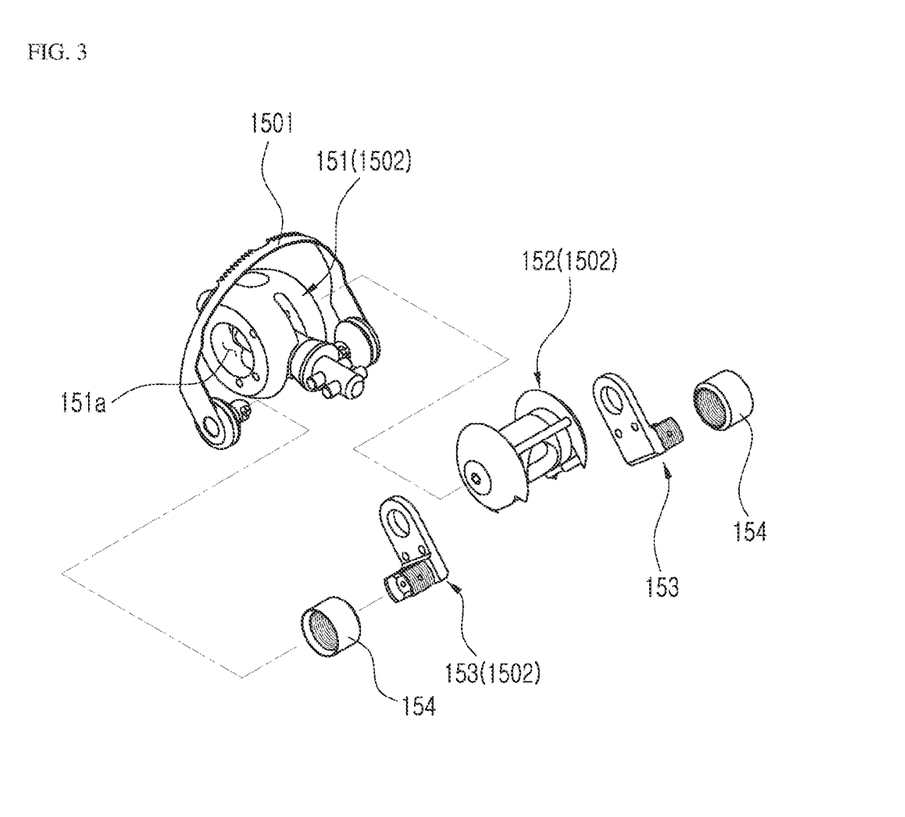
FIG. 3 is an exploded perspective view schematically showing a cutting part of the acetabular cup removing apparatus for an artificial hip joint of FIG. 1.
Figure 4:
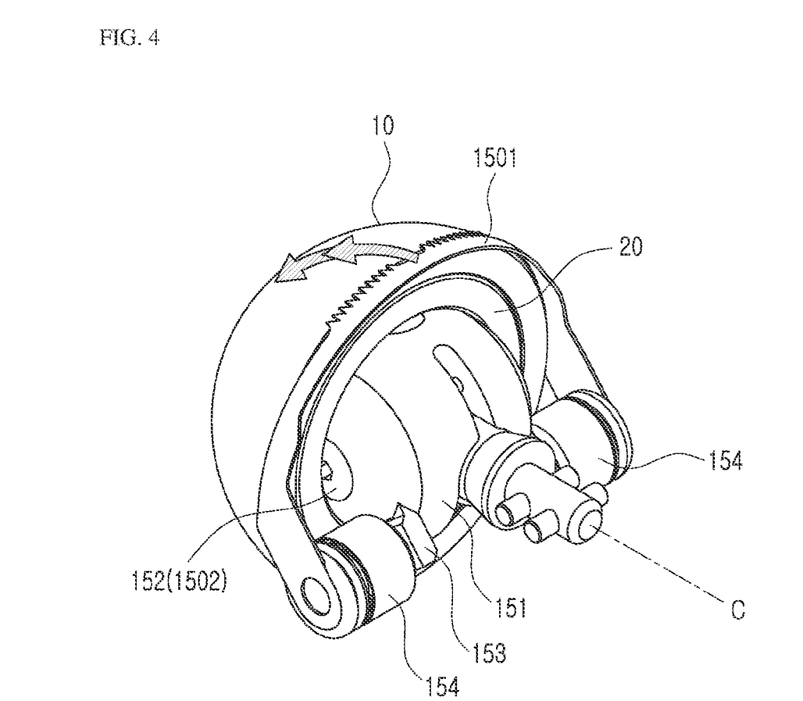
FIG. 4 is an assembly perspective view schematically showing the cutting part of the acetabular cup removing apparatus for an artificial hip joint of FIG. 1, schematically showing a state in which an acetabular cup is added to adjust an angle of a rotating cutter along an outer peripheral surface of the acetabular cup.

For example, the cutter 1501 is tiltable along the acetabular portion by the cutter tilting unit 1502. In detail, the cutter tilting unit 1502 may include a first tilting member 151, a second tilting member 152, and a connection bracket 153, as shown in FIGS. 3 and 4.

The first tilting member 151 is provided at the front end of the main shaft 120 and includes a hinge hole 151a formed in a direction orthogonal to the central axis of the main shaft 120. The second tilting member 152 is pivotably inserted into the hinge hole 151a, and one end of a power transmission arm 148 of a power transmission member 144, which will be described below, is pivotably connected thereto. The connection bracket 153 is an element that forms a cutting trajectory (approximately a hemispherical trajectory) corresponding to the acetabular portion during a rotation of the main shaft 120 and concurrent tilting of the cutter 1501, and may have a letter "L" shape. In an example, one end of the connection bracket 153 may be fixed to one end of the second tilting member 152, and the other end of the connection bracket 153 may be fixed to the cutter 1501. For reference, in FIG. 3, a reference numeral "154" denotes a coupling means for coupling the cutter 1501 with the connection bracket 153, and in FIG. 4, a reference numeral 10 denotes the acetabular cup, and a reference numeral 20 denotes a "support cup" for supporting the first tilting member 151 in the acetabular cup 10, respectively.

As shown in FIGS. 1, 2 and 6, the stepless adjustment unit 140 is an element that steplessly adjusts the tilting angle of the cutter tilting unit 1502 while continuously moving along the main shaft 120 in the forward and backward direction (up and down direction based on FIG. 6). With this stepless adjustment unit 140 being provided, unlike the conventional example, there is no steps divided and as a result, the surface of the acetabular portion can be evenly cut, the cutter 1501 can be directly located at a position that requires more cutting of the acetabular portion with the forward and backward movement, and the tilting angle of the cutter 1501 can be adjusted to the immediately previous angle, thereby ensuring convenience of use and shortened procedure time.

The stepless adjustment unit 140 may include a slider 141, a handle fixing clamp 142, the bearing part 143, and the power transmission member 144. In an example, the slider 141 and the power transmission member 144 may be integrally formed.

The slider 141 may be moved relative to the main shaft 120 in the forward and backward direction on the outer peripheral surface of the main shaft 120 to push the power transmission member 144, which is in contact with the front end of the slider 141, in a forward direction so that the cutter unit 150 is tilted. As described above, the force that causes the tilting of the cutter unit 150 may be sequentially transmitted to the cutter 1501 by a power transmission arm 1442 of the power transmission member 144, a second tilting member 152 of the cutter tilting unit 150 to which one end of the power transmission arm 1442 are connected, and the connection bracket 153 connected to one end of the second tilting member 152. For reference, in order to indicate the position of the slider 141 that is disposed around the main shaft 120, FIGS. 2 and 6 show the slider 141 separated apart from the acetabular cup removing apparatus, in dotted lines extending from the front and rear ends of the slider 141.

The handle fixing clamp 142 is an element to which the second handle 170 is fixed, and includes a front cover 147 installed at the front end thereof. Meanwhile, a rear cover 146 is located at the rear end of the handle fixing clamp 142, in which the rear cover 146 supports the handle fixing clamp 142 to keep it 142 from being pushed backward, and to this end, the rear cover 146 may be fixed to the main shaft 120, for example.

The rear end of the slider 141 is connected to the front end of the handle fixing clamp 142. In an example, the rear end of the slider 141 is coupled so as not to come off from the front cover 147 of the handle fixing clamp 142 (for example, by forming the diameter of the rear end of the slider to be greater than the inner diameter of the front cover so that the rear end of the slider is locked in the front cover), and is rotatably coupled with respect to the main shaft 120.

The bearing part 143 (143a, 143b, 143c, and 143d) may be disposed to allow a smooth rotation of the main shaft 120 and the slider 141 that are rotatable relative to the handle fixing clamp 142. For example, at the front end portion of the handle fixing clamp 142, a bearing 143a may be disposed between the handle fixing clamp 142 and the slider 141, and a bearing 143b may be disposed between the handle fixing clamp 142 and the main shaft 120. In addition, at a rear end portion of the handle fixing clamp 142, a bearing 143c may be disposed immediately in front of the rear cover 146. In addition, a thrust bearing 143d may be disposed between the handle fixing clamp 142 and the main shaft 120, to push the rear end of the slider 141 with the load acting in the axial direction as the stepless adjustment unit 140 is moved forward. The above arrangement of the bearing part is merely exemplary and is not limited thereto, and accordingly, the bearings may be arranged in various ways for smooth rotation of the main shaft 120 and the slider 141 relative to the handle fixing clamp 142, and for smooth movement of the stepless adjustment unit 140 in the forward and backward direction.

The power transmission member 144 transmits the push force (moving force) of the slider 141 to the second tilting member 152 of the cutter tilting unit 1502. Specifically, the power transmission member 144 includes a power transmission member body part 1441 that surrounds the main shaft 120 to be slidable relative to the main shaft 120 and is in contact with the front end of the slider 141, and a power transmission arm 1442 pivotably connected at one end to the power transmission member body part 1441 and pivotally connected at the other end to the cutter tilting unit 1502.

Figure 5:
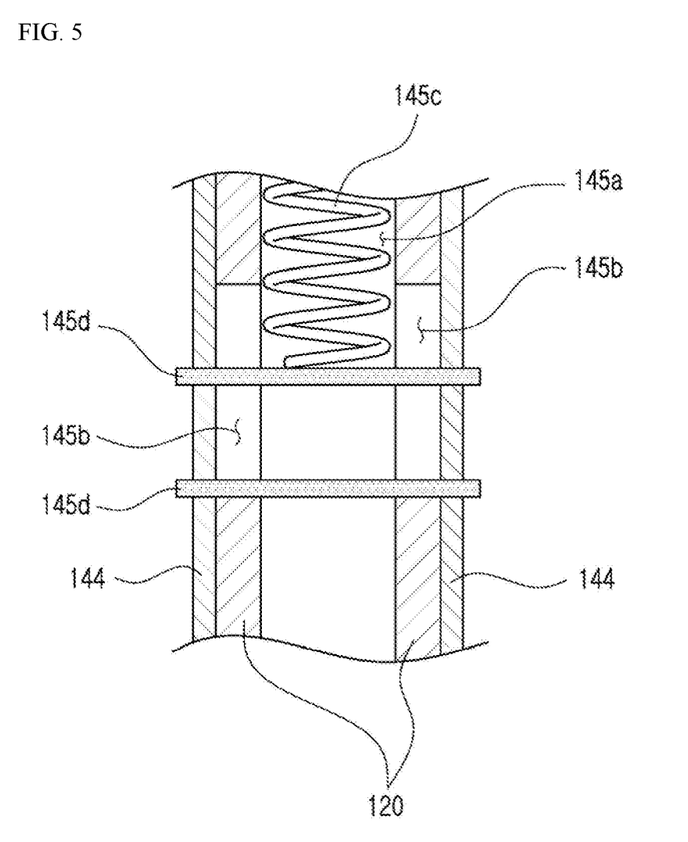
FIG. 5 is a cross-sectional view showing the acetabular cup removing apparatus for an artificial hip joint of FIG. 1 taken along V-V line.

In addition, the power transmission member 144 may further include an elastic supporting part 145 for elastically supporting the power transmission member 144 with respect to the main shaft 120, as shown in FIGS. 2, 5 and 6. Therefore, when the slider 141 is moved forward, pushing the power transmission member 144 forward, the power transmission member 144 may press the elastic supporting part 145 and be moved slowly rather than being moved rapidly, thereby allowing a more precise control of the tilting angle of the cutter 1501. In addition, when the operator wants to move the stepless adjustment unit 140 backward, the slider 141 and the stepless adjustment unit 140 may be retracted by the elastic supporting part 145 without requiring a separate force to be applied on the stepless adjustment unit 140 in the rear direction, thereby further ensuring the convenience of the procedure.

For example, as shown in FIG. 5, the elastic supporting part 145 may include a hollow part 145a, a guide groove 145b, an elastic body 145c, and a connection member 145d. The hollow part 145a is a place where the elastic body 145c is placed, and may be formed on the main shaft 120 in the longitudinal direction. The guide groove 145b may be formed to penetrate a side of the main shaft 120 to guide the movement of the connection member 145d and may be connected to the hollow part 145a to communicate therewith. The elastic body 145c may be inserted into the hollow part 145a, and the connection member 145d may have a bar shape to connect the power transmission member 144 with the elastic body 145c through the guide groove 145b. In an example, a coil spring or the like may be used as the elastic body 145c.

In particular, as shown in FIGS. 5 and 6, by being connected with the first tilting member 151, one end of the hollow part 145a may be kept in a closed (blocked) state. In addition, one end of the elastic body 145c may be supported by the closed one end of the hollow part 145a, and the other end of the elastic body 145c may be supported by the connection member 145d. In addition, the length of the guide groove 145b may be determined so as to guide the movement of the connection member 145d in accordance with the movement range of the power transmission member 144 in the forward and backward direction.

Meanwhile, it is described in an exemplary embodiment that the slider 141 is a discrete element that is separated from the power transmission member 144, but the slider 141 and the power transmission member 144 may be integrally formed.

Hereinafter, the operation of the present disclosure having the configuration as described above will be described. FIG. 7 shows the stepless adjustment unit 140 being moved forward, resulting in the cutter 1501 being sequentially tilted forward (in counterclockwise direction). In this example, FIG. 7A may correspond to FIG. 2 and FIG. 7C may correspond to FIG. 6, respectively.

In a state shown in FIGS. 1 and 2, when the main driving unit 110 is operated, the main shaft 120 is rotated, and the cutter tilting unit 1502 connected to the main shaft 120 is also rotated. The power transmission member 144 is also rotated by the power transmission arm 1442 connected to the cutter tilting unit 1502. At this time, the slider 141 in contact with the rear end of the power transmission member 144 may also be rotated. The slider 141 may be rotated relative to the handle fixing clamp 142 by the bearing 143a.

Next, as shown in FIG. 6, in order to tilt the cutter 1501 as desired, the second handle 170 is pushed forward to move the handle fixing clamp 142 forward. As a result, the thrust bearing 143d of the stepless adjustment unit 140, which is in contact with the rear end of the slider 141, pushes the slider 141 securely connected to the handle fixing clamp 142, followed by the slider 141 pushing the power transmission member 144 and then the power transmission arm 1442 tilting the cutter tilting unit 1502, which causes the cutter 1501 to tilt together. Meanwhile, when the power transmission member 144 is moved forward, the connection member 145d interlocked therewith is also moved forward and compress the elastic body 145c, and at this time, in order to tilt the cutter 1501 to the state as shown in FIG. 7B, reducing the force that pushes the second handle 170 forward may cause the cutter 1501 to be automatically tilted backward by a predetermined angle by the elastic force of the elastic body 145c.

As described above, according to the present disclosure, the stepless adjustment unit can steplessly adjust the tilting angle of the cutter while continuously moving in a forward and backward direction along the main shaft, and unlike the conventional one, there is no steps divided, thereby ensuring even cutting of the surface of the acetabular portion.

In addition, by moving the stepless adjustment unit in the forward and backward direction, the cutter can be located directly at a position requiring more cutting of the acetabular portion, and the tilting angle of the cutter can be adjusted to the immediately previous angle, thereby ensuring ease of use and shortened procedure time, and it is also expected to provide a positive effect of shortened recovery time of a patient.

The present disclosure has been described in detail, however, it should be understood that the detailed description and specific examples, while indicating preferred embodiments of the disclosure, are given by way of illustration only, since various changes and modifications within the scope of the disclosure will become apparent to those skilled in the art from this detailed description.

INDUSTRIAL APPLICABILITY

The present disclosure can be used to remove an acetabular cup for an artificial hip joint.

What is claimed is:

1. An acetabular cup removing apparatus for an artificial hip joint, the acetabular cup removing apparatus comprising:
   a power tool comprising a main driving motor, a battery for supplying power to the main driving motor, and a first handle;
   a main shaft rotatable by a driving force of the main driving motor;
   a cutter unit disposed at a front end of the main shaft, wherein the cutter unit is tiltable along an acetabular portion into which an acetabular cup has been implanted, and cuts the acetabular portion by rotating around an imaginary extension line of a longitudinal axis of the main shaft while being rotated by the main shaft; and
   a stepless adjustment unit continuously moved in a forward and backward direction relative to the main shaft to steplessly adjust a tilting angle of the cutter unit;
   wherein the stepless adjustment unit includes:
   a slider movable relative to the main shaft on an outer peripheral surface of the main shaft in a forward and backward direction;
   a handle fixing clamp of which a front end is connected with a rear end of the slider in a manner in which the rear end of the slider is retained, wherein the handle fixing clamp is movable relative to the main shaft;

a second handle fixed to the handle fixing clamp, the second handle and the handle fixing clamp being stationary relative to one another; and a power transmission member for tilting the cutter unit by transmitting a moving force of the slider;

wherein the handle fixing clamp is movable by application of force to the second handle to push the power transmission member in a direction to cause a cutter of the cutter unit to tilt, wherein the power transmission member includes:

a power transmission member casing surrounding the main shaft while being slidable relative to the main shaft; and a power transmission arm pivotably connected at one end to the power transmission member casing and pivotably connected at another end to the cutter unit to tilt the cutter unit, wherein the power transmission member further includes an elastic supporting part for elastically supporting the power transmission member casing with respect to the main shaft, wherein the elastic supporting part includes:

a hollow part formed on the main shaft in a longitudinal direction thereof;

a guide groove formed to penetrate a side of the main shaft and communicate with the hollow part;

a spring inserted into the hollow part of the main shaft; and a connection bar for connecting the power transmission member casing with the spring through the guide groove, and wherein one end of the hollow part is kept in a closed state, one end of the spring is supported by the one end of the hollow part, and another end of the spring is supported by the connection bar.

2. The acetabular cup removing apparatus for an artificial hip joint according to claim 1, wherein the stepless adjustment unit further includes a bearing part for allowing the main shaft and the slider to rotate smoothly relative to the handle fixing clamp.

3. The acetabular cup removing apparatus for an artificial hip joint according to claim 2, wherein the bearing part includes:

at a front portion of the handle fixing clamp, a first bearing disposed between the handle fixing clamp and the slider, and a second bearing disposed between the handle fixing clamp and the main shaft; and at a rear portion of the handle fixing clamp, a third bearing disposed between the handle fixing clamp and the main shaft; and a thrust bearing disposed between the handle fixing clamp and the main shaft.

4. The acetabular cup removing apparatus for an artificial hip joint according to claim 1, wherein a rear cover is located at a rear end of the handle fixing clamp to support the handle fixing clamp so that the handle fixing clamp is kept from being pushed backward, and the rear cover is fixed to the main shaft.

5. The acetabular cup removing apparatus for an artificial hip joint according to claim 1, wherein the cutter unit includes the cutter and a cutter tilting unit for tilting the cutter, and wherein the cutter tilting unit includes:

a first tilting hinge part connected to a front end of the main shaft and including a hinge hole in a direction orthogonal to an axial direction of the main shaft;

a second tilting hinge part rotatably inserted into the hinge hole and to which the other end of the power transmission arm is pivotably connected; and a connection bracket connected at one end to the second tilting hinge part and connected at another end to the cutter to form a cutting trajectory corresponding to the acetabular portion while the main shaft is being rotated and the cutter is being tilted.

6. The acetabular cup removing apparatus for an artificial hip joint according to claim 1, wherein the slider and the power transmission member may be integrally formed.

* * * * *